United States Patent [19]
Mannschedel

[11] Patent Number: 5,925,179
[45] Date of Patent: Jul. 20, 1999

[54] ELASTIC-PLASTIC ELEMENT FOR FILLING ROOT CANALS AND A PREPARATION METHOD

[75] Inventor: Werner Mannschedel, Langenau, Germany

[73] Assignee: Roeko GmbH + Co. Dentalerzeugnisse, Langenau, Germany

[21] Appl. No.: 08/860,637

[22] PCT Filed: Jan. 18, 1996

[86] PCT No.: PCT/EP96/00192

§ 371 Date: Jul. 17, 1997

§ 102(e) Date: Jul. 17, 1997

[87] PCT Pub. No.: WO96/22069

PCT Pub. Date: Jul. 25, 1996

[30] Foreign Application Priority Data

Jan. 18, 1995 [DE] Germany .......................... 195 01 374

[51] Int. Cl.$^6$ ............................. A61K 6/00; A61K 49/04; A61C 5/04; A61C 27/00
[52] U.S. Cl. ............................. 106/35; 523/115; 523/116; 523/117; 433/228.1; 526/335; 524/436
[58] Field of Search .............................. 106/35; 523/115, 523/116, 117; 433/228.1; 526/335; 524/436

[56] References Cited

U.S. PATENT DOCUMENTS

| | | | |
|---|---|---|---|
| 4,483,678 | 11/1984 | Fujisawa et al. | 433/228 |
| 4,632,977 | 12/1986 | Riazi | 528/502 |
| 4,657,592 | 4/1987 | Takubo | 106/35 |
| 4,740,245 | 4/1988 | Futami et al. | 106/35 |
| 5,540,766 | 7/1996 | Castellani | 106/35 |
| 5,648,403 | 7/1997 | Martin | 523/117 |

FOREIGN PATENT DOCUMENTS

| | | |
|---|---|---|
| 3628823 | 3/1987 | Germany . |
| 1060275 | 3/1967 | United Kingdom . |

OTHER PUBLICATIONS

Briseno, "Die Thermoplastischen Wurzelkanalfullmethoden im Uberblick", Philipp J., vol. 2 (90), pp. 65–73, 1990 no month.

Friedman et al., "Composition and Mechanical Properties of Gutta–Percha Endodontic Points," Journal of Dental Research, vol. 54, No. 5, (Sep.–Oct., 1975) pp. 921–925.

*Primary Examiner*—Melissa Kaslow
*Attorney, Agent, or Firm*—Brooks & Kushman P.C.

[57] ABSTRACT

The invention relates to an elastic-plastic element comprising an isoprene-based matrix and at least one filler, the element being suitable for filling root canals of humans or animals and being characterised by calcium hydroxide, incorporated into the matrix, as filler. The invention relates also to a method of preparing the element according to the invention.

4 Claims, No Drawings

ELASTIC-PLASTIC ELEMENT FOR FILLING ROOT CANALS AND A PREPARATION METHOD

The present invention relates to an elastic-plastic element comprising an isoprene-based matrix and at least one filler, the element being suitable for filling root canals of humans or animals. The invention relates also to a method of preparing the elastic-plastic element.

In the treatment of the disorder known as pulpitis, the diseased pulpa is removed mechanically from the root canal and the root canal is cleaned and drilled out, filled with an elastic-plastic element or with a different filling material and then sealed. For the prior art, see, for example, Friedman et al. in J. Dent. Res., 54 (1975) 921–925, Briseno in Philipp J. 2.98 (1990) and U.S. Pat. No. 4,632,977. As root canal filling materials, Briseno describes, inter alia, semi-rigid cements based on synthetic resin, zinc oxide eugenol or on calcium hydroxide. U.S. Pat. No. 4,632,977 proposes filling materials based on trans-polyisoprene, for example based on gutta-percha or balata. Gutta-percha points are commercially available, the standard composition thereof being 20% by weight of gutta-percha as matrix, from 60 to 75% by weight of zinc oxide as filler, from 1 to 17% by weight of heavy metal sulphates as X-ray contrast agent and from 3 to 4% by weight of waxes and resins as plasticizer. That known filling material is inert in the root canal and accordingly does not react with body tissue.

During the filling of a root canal with a known inert filling material, it cannot, however, be ruled out that, for example as a result of germs remaining in the canal, after the filling operation an inflammatory process may slowly develop which renders further treatment necessary, often resulting in complete loss of the tooth.

In view of the prior art, the problem underlying the present invention is to provide an elastic-plastic element for filling root canals of humans or animals that can be prepared and processed readily and simply and is not subject to the adverse effects mentioned. The problem underlying the present invention is also to provide a method of preparing such an element.

That problem is solved according to an embodiment of the invention by an elastic-plastic element comprising an isoprene-based matrix and at least one filler, the element being suitable for filling root canals of humans or animals and being characterised by calcium hydroxide, incorporated into the matrix, as filler.

Calcium hydroxide can be processed readily with an isoprene-based matrix, such as gutta-percha, it being advantageous to roll in the calcium hydroxide in the form of a powder, which simplifies the preparation process substantially.

Since calcium hydroxide has an alkaline action, it is able to buffer the acids that form in inflammatory processes and is able to limit a rise in the pH value. As a result, the healing process is advantageously accelerated and assisted. The insert can remain in the root canal temporarily or for a prolonged period of time.

According to the invention, a matrix based on trans-polyisoprene, gutta-percha and/or on balata may be provided. The matrix may be characterised by at least 80% by weight of trans-polyisoprene.

The elastic-plastic element according to the invention may be in the form of a gutta-percha point.

The calcium hydroxide used as filler according to the invention may be provided in the form of a mixture with a customary, different filler, such as zinc oxide, or may be provided as sole filler. The filler is preferably more of calcium silicate.

Of course, the elastic-plastic element according to the invention may comprise additionally a pharmaceutical active ingredient, especially an active ingredient that is soluble or dispersible in an aqueous medium, for example an antibiotic and/or glucocorticoid, and also a customary X-ray contrast agent and customary waxes, resins or other excipients. An elastic-plastic element according to the invention may be characterised preferably by:

(a) from 43.5 to 65.0% by weight of matrix,
(b) from 35.0 to 56.5% by weight of filler,
(c) optionally additionally up to 8% by weight of X-ray contrast agent, based on (a) and (b), and
(d) optionally additional customary components.

For example, the elastic-plastic element according to the invention may be characterised, for example, by (a) approximately 43.5% by weight of gutta-percha,
(b) approximately 56.5% by weight of calcium hydroxide as sole inorganic filler,
(c) optionally additionally up to 8% by weight of X-ray contrast agent, based on (a) and (b), and
(d) optionally additional customary components.

The elastic-plastic element according to the invention has, accordingly, essentially three components which will be explained in greater detail hereinafter.

Component 1

The mechanical properties of an elastic-plastic element according to the invention are determined primarily by the properties of the matrix, which makes up, for example, from 43.5 to 65.0% by weight together with from 35.0 to 56.5% by weight of filler (component 2). The matrix must, on the one hand, be elastic so that it can be processed easily and introduced readily into the root canal. On the other hand, it should have plastic properties so that the root canal can be completely filled permanently without a gap being left at the wall. Moreover, the matrix must be able to take up other components, especially the filler, readily. For those purposes, a matrix having at least 80% by weight of trans-polyisoprene has proved advantageous. Gutta-percha may be mentioned by way of example, which is a naturally-based matrix, the main component of which is trans-polyisoprene. Of course, other trans-polyisoprenes can also be used, such as balata, isoprene-based synthetic materials or derivatives of the mentioned materials.

Component 2

The elastic-plastic element according to the invention is characterised by calcium hydroxide as filler. The filler is present, for example, in an amount of from 35.0 to 56.5% by weight together with from 43.5 to 65.0% by weight of matrix. Calcium hydroxide is a substance that is tolerated by tissue and by the body and can be mixed with the matrix and compounded additionally with pharmaceutical active ingredients and customary excipients.

Calcium hydroxide can be rolled in powder form into gutta-percha, which renders the preparation process very simple.

As already stated, calcium hydroxide is able to buffer the pH rise that usually occurs in inflammatory processes. It is therefore desirable to introduce as much calcium hydroxide as possible into the root canal. The amount of calcium hydroxide in the elastic-plastic element according to the invention is accordingly guided by that desire, on the one hand, and by the capacity of the matrix to take up the inorganic filler, on the other. An example of an elastic-plastic element having a very high filler content is a gutta-percha point having a content of approximately 56.5% by weight of calcium hydroxide together with approximately 43.5% by weight of gutta-percha.

Component 3

A further, optional (although customary) component that may be provided is an X-ray contrast agent, for example a heavy metal sulphate, such as barium sulphate, or a bismuth/strontium compound. The component may be provided in an amount of up to 8% by weight, based on matrix and filler.

Finally, according to a further embodiment of the invention, there is provided a method of preparing an elastic-plastic element according to the invention, characterised by:

(a) forming a film of an isoprene-based matrix;
(b) rolling into the matrix film at least one filler and optionally also an X-ray contrast agent and further optional customary excipients, preferably in powder form or in a form that is not too highly viscous;
(c) comminuting and extruding the compounded film; and
(d) cutting up the extruded material and rolling the cut piece to form elastic-plastic elements that are suitable for filling root canals of humans or animals.

The invention will be illustrated hereinafter by an Example.

EXAMPLE

To prepare gutta-percha points, first, gutta-percha as matrix is rolled between a support roller and a pressure roller so that the gutta-percha lies around the support roller in the form of a thin film or in the manner of a skin. Calcium hydroxide in powder form in a weight ratio of 56.5% $Ca(OH)_2$: 43.5% gutta-percha is subsequently rolled into the film that has been formed, the film is peeled away from the support roller, and the peeled-off film is comminuted and extruded to form a thin wire-like strand. The strand is then cut up and rolled.

The resulting elastic-plastic elements can be introduced readily into root canals and are positioned without canalization.

I claim:

1. An elastic-plastic element comprising an isoprene-based matrix and a calcium hydroxide-containing filler, said filler free of calcium silicate, the element being suitable for filling root canals of humans or animals, comprising:
   (a) from 43.5 to 65.0% by weight of matrix,
   (b) from 35.0 to 56.5% by weight of filler,
   (c) optionally up to 8% by weight of X-ray contrast agent, based on (a) and (b), and
   (d) optionally additional customary components, wherein said filler comprise a mixture of zinc oxide and calcium hydoxide.

2. A method of preparing an elastic-plastic element, suitable for filling root canals of humans or animals, comprising from 43.5 to 65.0% by weight of an isoprene-based matrix; from 35.0 to 56.5% by weight of a calcium hydroxide containing filler, where the filler is free of calcium silicate; optionally up to 8% by weight of X-ray contrast agent, based on the matrix and filler; and optionally additional customary components, said method comprising
   (a) forming a film of an isoprene-based matrix,
   (b) rolling into the matrix film at least one filler and optionally an X-ray contrast agent and/or further optional customary components,
   (c) comminuting and extruding the compounded film, and
   (d) cutting up the extruded material into cut pieces and rolling said pieces to form elastic-plastic elements that are suitable for filling root canals of humans or animals.

3. An elastic-plastic element comprising an isoprene-based matrix and a calcium hydroxide-containing filler, said filler free of calcium silicate, the element being suitable for filling root canals of humans or animals, comprising:
   (a) from 43.5 to 65.0% by weight of matrix,
   (b) from 35.0 to 56.5% by weight of filler,
   (c) optionally up to 8% by weight of X-ray contrast agent, based on (a) and (b), and
   (d) optionally additional customary components, wherein said isoprene-based matrix is selected from the group consisting of trans-polyisoprene, gutta-percha, balata, and mixtures thereof and wherein said calcium hydroxide-containing filler comprises calcium hydroxide and zinc oxide.

4. An elastic-plastic element comprising an isoprene matrix and a calcium hydroxide-containing fillers wherein said filler comprises calcium hydroxide, the element being suitable for filling root canals of humans or animals, comprising:
   (a) from 43.5 to 65.0% by weight of matrix,
   (b) from 35.0 to 56.5% by weight of filler,
   (c) optionally up to 8% by weight of X-ray contrast agent, based on (a) and (b), and
   (d) optionally additional customary components, wherein said isoprene matrix is selected from the group consisting of trans-polyisoprene, gutta-percha, balata, and mixtures thereof.

* * * * *